US00PP31606P2

(12) United States Plant Patent
Howell

(10) Patent No.: US PP31,606 P2
(45) Date of Patent: Mar. 31, 2020

(54) APPLE TREE NAMED 'HOWELL TC7'

(50) Latin Name: ***Malus domestica* Borkh.**
Varietal Denomination: Howell TC7

(71) Applicant: Howell Fruit Advantage, LLC, Prosser, WA (US)

(72) Inventor: William Edward Howell, Prosser, WA (US)

(73) Assignee: Howell Fruit Advantage, LLC, Prosser, WA (US)

( * ) Notice: Subject to any disclaimer, the term of this patent is extended or adjusted under 35 U.S.C. 154(b) by 0 days.

(21) Appl. No.: 16/350,849

(22) Filed: Jan. 22, 2019

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

'Howell TC7' is a new and distinct apple tree notable for its distinctive fruit, which has yellow-green skin with pink overcolor, red and white flesh and an appealing sweet/tart flavor.

3 Drawing Sheets

Latin name of the genus and species of the plant claimed: *Malus domestica* Borkh.
Variety denomination: 'Howell TC7'.

BACKGROUND OF THE INVENTION

The new variety of apple tree named 'Howell TC7' was created in the course of a planned breeding program carried out in Prosser, Wash. 'Howell TC7' originated as a result of an open pollination cross in 2001 of 'Airlie Red Flesh' (seed parent, not patented) and 'Honeycrisp' (U.S. Plant Pat. No. 7,197, expired) as the likely pollen parent. 'Howell TC7' was selected in 2013 as a single plant from among a population of seedlings derived from the parents, and was selected for its quality of fruit and the white and red color of the fruit flesh. It is distinguished from its parents by its yellow-green skin color with pink overcolor, white and red flesh color, and appealing fruit flavor. Asexual propagation by budding was first carried out In Prosser, Wash. The variety has since been observed over a number of asexually propagated generations, and has been found to remain true to type.

BRIEF SUMMARY OF THE INVENTION

'Howell TC7' is a new and distinct apple tree notable for its distinctive fruit, which has yellow-green skin with pink overcolor, red and white flesh, and an appealing sweet/tart flavor. A comparison of 'Howell TC7' to related and similar varieties is shown in Table 1 below.

TABLE 1

Comparison of 'Howell TC7' to Related and Similar varieties

| | 'Howell TC7' | 'Airlie's Red Flesh' | 'Honeycrisp' | 'Howell TC2'* |
|---|---|---|---|---|
| Bloom Color | Pink | Dark pink | White | Pink |
| Flesh Color | Red, white | Pink | White | Red, white |

TABLE 1-continued

Comparison of 'Howell TC7' to Related and Similar varieties

| | 'Howell TC7' | 'Airlie's Red Flesh' | 'Honeycrisp' | 'Howell TC2'* |
|---|---|---|---|---|
| Skin Color | Yellow-green with pink overcolor | Light green | Green with red overcolor | Yellow with red overcolor |
| Tree Vigor | Moderate | Moderate | Non-vigorous | Non-vigorous |

*'Howell TC2' - U.S. Plant Pat No. 28,545

BRIEF DESCRIPTION OF THE PHOTOGRAPH

Figure 1:
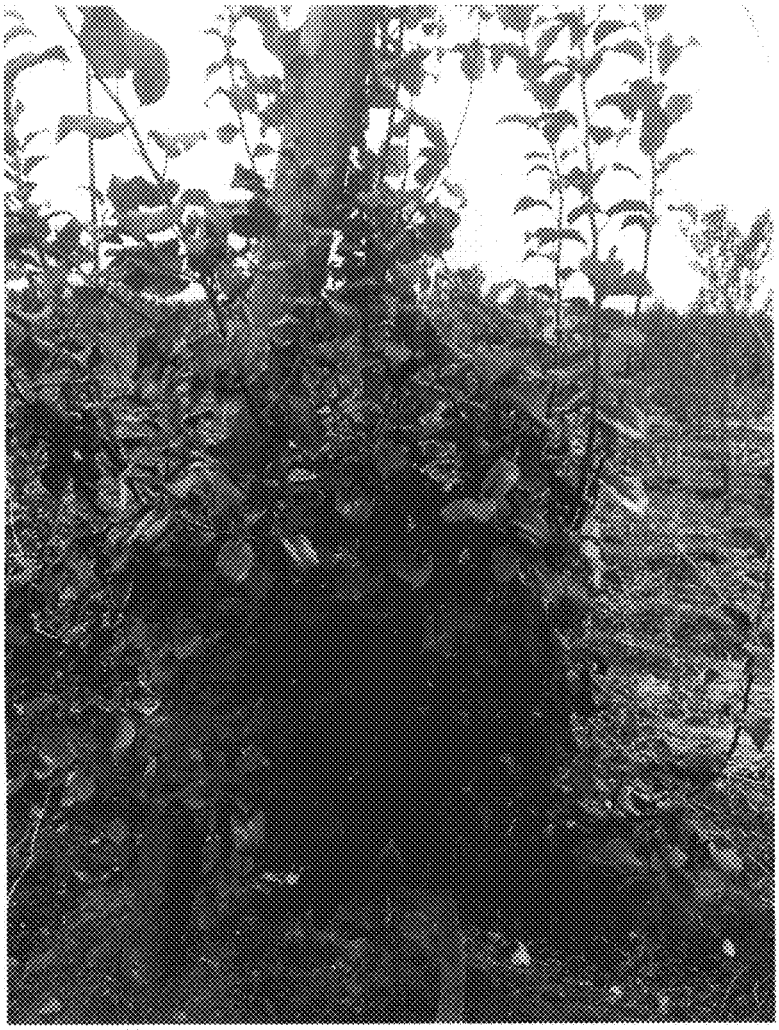
Figure 2:
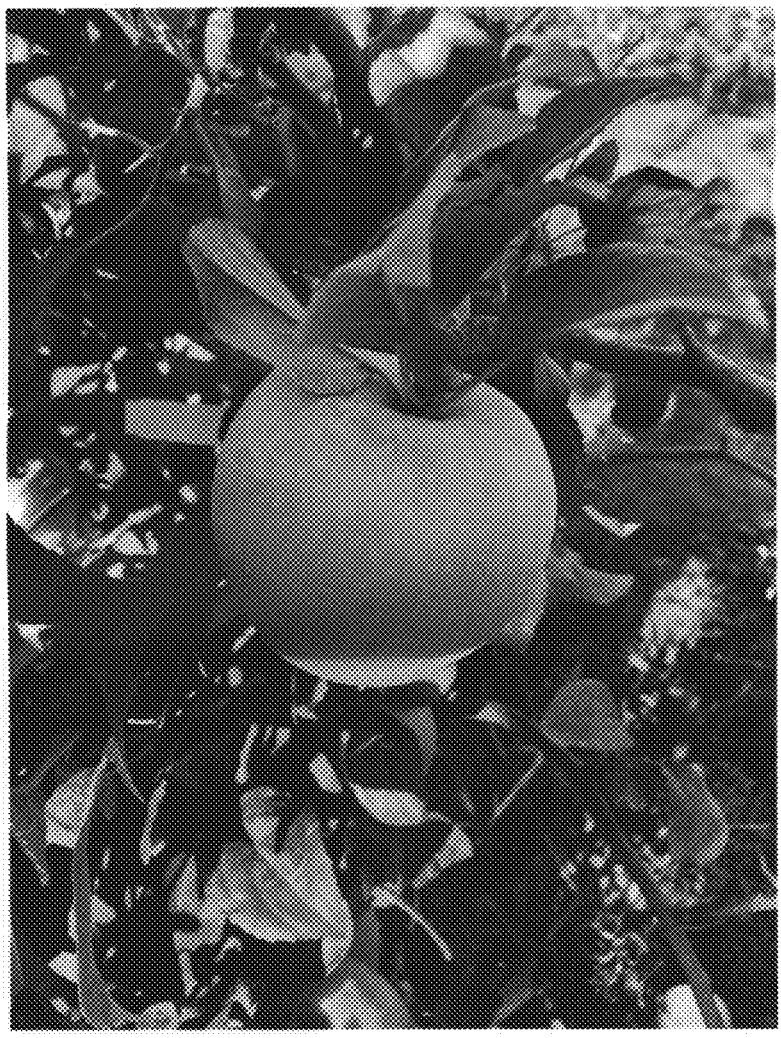
Figure 3:
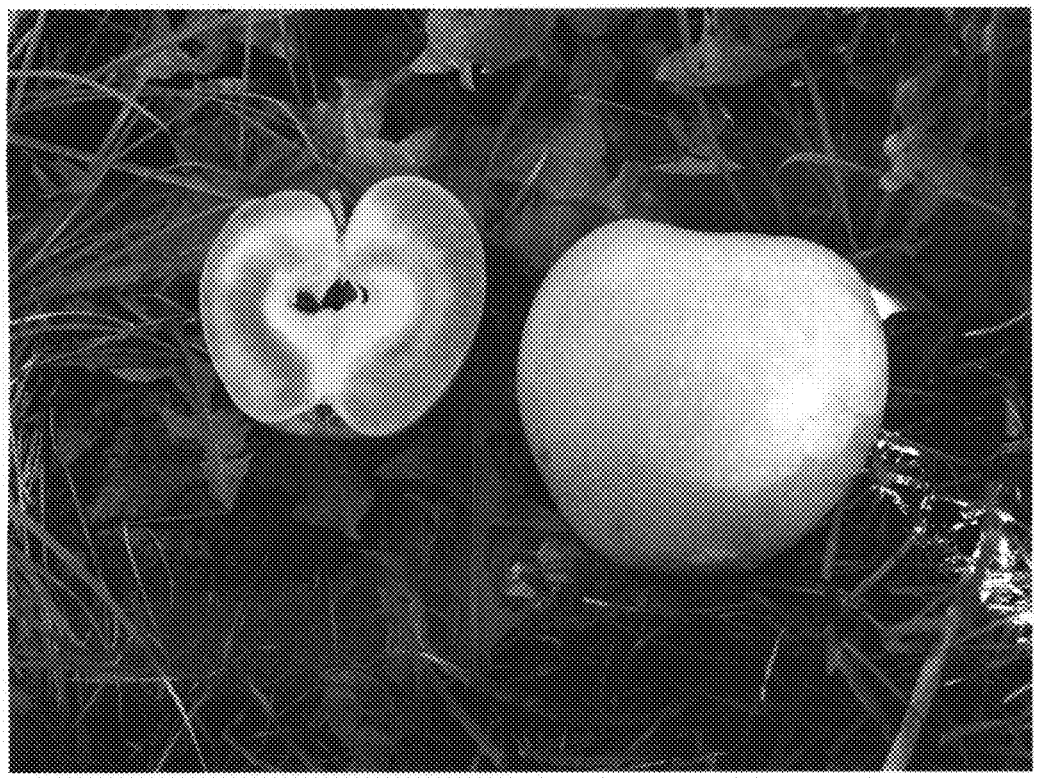

FIG. 1 shows a tree of the new variety;
FIG. 2 shows the fruit of the new variety on the tree; and
FIG. 3 shows a sectioned fruit of the new variety.

DETAILED BOTANICAL DESCRIPTION

The following detailed botanical description is based on observations made during the 2018 growing season at Prosser and Wapato, Wash. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor.*—Moderate.
*Habit.*—Semi-spreading.
*Height.*—2.5 m.
*Diameter.*—1.3 m.
*Trunk diameter.*—7 cm (measured at 30 cm above the graft).

*Bark texture*.—Rough.
*Bark color*.—Greyed-orange N170B.
*Lenticel size*.—7 mm.
*Lenticel color*.—Orange-white 159B.
*Winter hardiness*.—Hardy in area tested (USDA Zone 6B).

Branch (fruiting branches located at around 1 m above the graft):
*Length*.—31 cm.
*Crotch angle*.—70°.
*Color*.—Greyed-orange 174B.
*Lenticel size*.—0.3 cm.
*Lenticel color*.—Orange-white 159B.
*Lenticel density*.—9 per square cm.

One-year-old shoot:
*Length*.—46 cm.
*Diameter*.—0.5 cm.
*Internode length*.—3.5 cm.
*Color*.—Greyed-orange 166A.
*Lenticel size*.—0.1 cm.
*Lenticel color*.—White 155C.
*Lenticel density*.—7 per square cm.

Flower buds:
*Quantity per spur*.—5.
*Shape*.—Rounded.
*Length*.—1.2 cm.
*Diameter*.—0.7 cm.
*Color*.—Red-purple 63B.

Flowers:
*Color* (*balloon stage*).—Red-purple 63B.
*Diameter of open flower*.—4.5 cm.
*Depth of open flower*.—0.5 cm.
*Relative position of petal margins*.—Not touching.
*Date of first bloom*.—April 4 (2018 growing season).
*Date of full bloom*.—April 10 (2018 growing season).

Petals:
*Quantity per flower*.—5.
*Shape*.—Obovate.
*Length*.—2.5 cm.
*Width*.—1.0 cm.
*Apex*.—Rounded.
*Base*.—Cuneate.
*Margin*.—Smooth.
*Color*.—Upper surface — White N155C near center; edges red 55C (pale reel, appears pink).
*Color*.—Lower surface — White N155C near tip; remainder red 55C (pale red, appears pink).

Pistils:
*Length*.—1.1 cm.
*Color*.—Yellow-green 145B.

Anthers:
*Quantity*.—16.
*Length*.—2 mm.
*Pollen color*.—Yellow 2D.

Stigma:
*Diameter*.—1 mm.
*Color*.—Yellow 2D.

Style:
*Length*.—1 cm.
*Color*.—Yellow-green 145B.

Ovary:
*Length*.—1 cm.
*Diameter*.—0.3 cm.
*Color*.—Green 143A.

Sepals:
*Quantity*.—5 per flower.
*Length*.—1.1 cm.
*Width*.—0.3 cm.
*Shape*.—Pointed.
*Color*.—Yellow-green 147D.

Pedicel:
*Length*.—2 cm.
*Diameter*.—0.1 cm.
*Color*.—Yellow-green 147D.

Leaves:
*Length*.—6 cm.
*Width*.—3.8 cm.
*Shape*.—Ovate.
*Apex*.—Acuminate.
*Base*.—Aequilateral.
*Margin*.—Serrate.
*Color*.—Upper surface — Green 137A.
*Color*.—Lower surface — Yellow-green 146D.
*Attitude*.—Upward.

Petiole:
*Length*.—2.5 cm.
*Diameter*.—0.1 cm.
*Color*.—Yellow-green 146D.

Fruit:
*Diameter*.—6.7 cm.
*Height*.—6.8 cm.
*Weight about*.—180 g.
*Shape in profile*.—Conic.
*Ribbing*.—None.
*Crowning at calyx end*.—Little to none.
*Aperture of eye*.—Closed.
*Depth of eye basin*.—0.5 cm.
*Width of eye basin*.—1.5 cm.
*Length of stalk*.—1.5 cm.
*Diameter of stalk*.—0.2 cm.
*Color of stalk*.—Yellow-green 145A.
*Width of stalk cavity*.—2 cm.
*Depth of stalk cavity*.—1 cm.
*Presence of russet*.—In stalk cavity only.
*Size of lenticels*.—1 mm.
*Bloom of skin*.—None.
*Greasiness of skin*.—None.
*Ground color of skin*.—Yellow-green 144C to yellow-green 154D.
*Over color of skin*.—Red 52D (pale red, appears pink).
*Amount of over color*.—90%.
*Intensity of over color*.—Light.
*Pattern of over color*.—Evenly distributed blush.
*Flesh texture*.—Fine.
*Juiciness*.—Medium.
*Flesh color*.—White 155A and red 52A.

Seeds:
*Quantity per fruit*.—10.
*Shape*.—Teardrop.
*Length*.—0.7 cm.
*Width*.—0.5 cm.
*Color*.—Brown 200D.

Harvest date: Two weeks after 'Honeycrisp' and 'Howell TC2'.
*Harvest date*.—Sep. 25, 2018.

Resistance to diseases/pests: None noted.
Susceptibility to diseases/pests: None noted.
Market use: Fresh, processed.

The invention claimed is:

1. A new and distinct apple tree as shown and described herein.

* * * * *